(12) United States Patent
Maschke

(10) Patent No.: US 7,845,852 B2
(45) Date of Patent: Dec. 7, 2010

(54) MEDICAL CUSHION

(75) Inventor: Michael Maschke, Lonnerstadt (DE)

(73) Assignee: Siemens Aktiengesellschaft, Munich (DE)

(*) Notice: Subject to any disclaimer, the term of this patent is extended or adjusted under 35 U.S.C. 154(b) by 51 days.

(21) Appl. No.: 12/378,802

(22) Filed: Feb. 19, 2009

(65) Prior Publication Data
US 2009/0213997 A1    Aug. 27, 2009

(30) Foreign Application Priority Data
Feb. 25, 2008   (DE) .................. 10 2008 011 014

(51) Int. Cl.
*H05G 1/00*   (2006.01)
(52) U.S. Cl. ..................................... 378/208
(58) Field of Classification Search .................. 378/4, 378/20, 68, 195, 209, 205, 207, 37
See application file for complete search history.

(56) References Cited

U.S. PATENT DOCUMENTS
2007/0280412 A1* 12/2007 Defreitas et al. .............. 378/37

* cited by examiner

*Primary Examiner*—Irakli Kiknadze

(57) ABSTRACT

A medical cushion is provided. The medical cushion has at least one x-ray positive and at least one electromagnetic marker and a soft filler material that yields to the force exerted by the weight of a patient and molds itself at least to some extent to the surface of the body of the patient is provided. The soft filler material is arranged in the cushion in such a manner that it lies between the surface of the body of the patient and at least one x-ray positive and at least one electromagnetic marker when the cushion is in use.

19 Claims, 2 Drawing Sheets

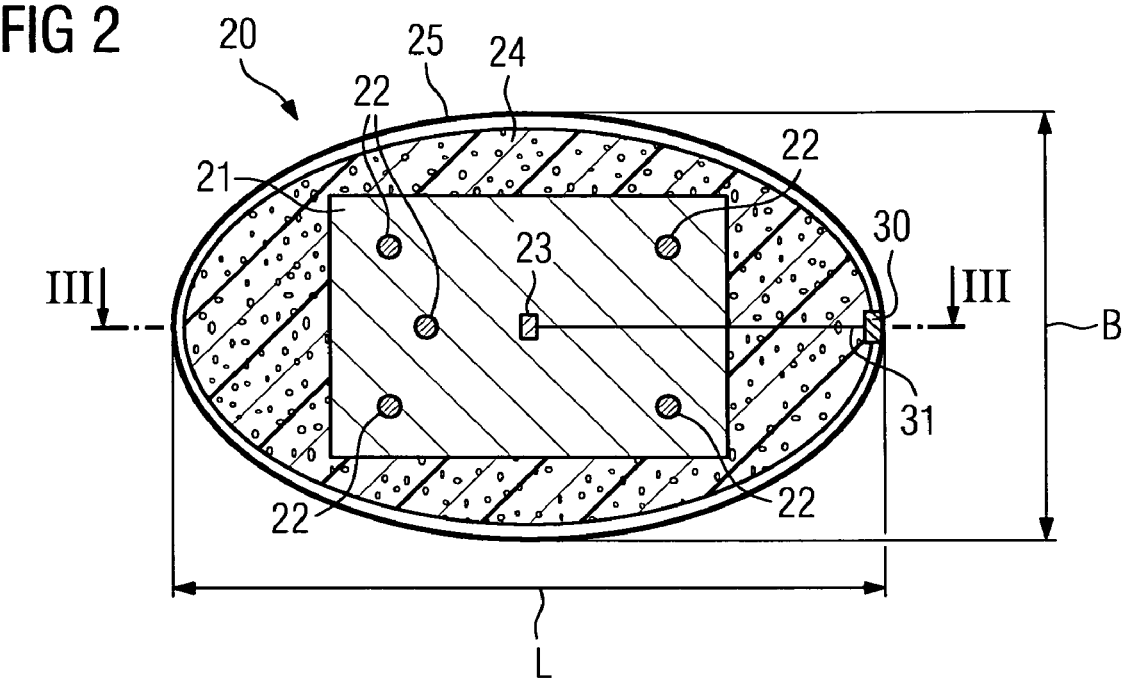
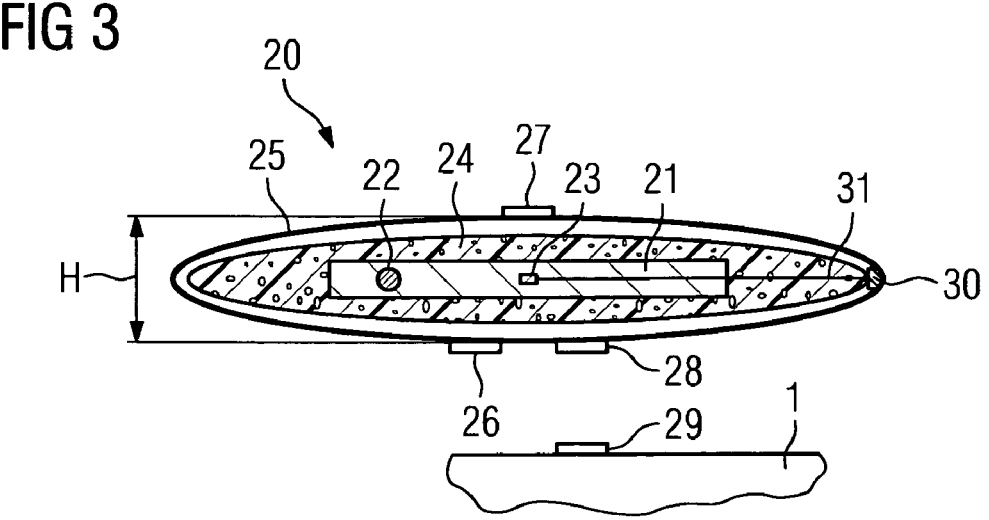

MEDICAL CUSHION

CROSS REFERENCE TO RELATED APPLICATIONS

This application claims priority of German application No. 10 2008 011 014.0 DE filed Feb. 25, 2008, which is incorporated by reference herein in its entirety.

FIELD OF INVENTION

The invention relates to a medical cushion for assisting with the navigation of a medical object inside the body of a patient.

BACKGROUND OF INVENTION

Minimally invasive medical interventions are used increasingly today. For example for the treatment of coronary heart disease, surgical bypass operations on the heart are to a large extent giving way to balloon dilatation (PTCA=percutaneous transluminal coronary angioplasty) and the deployment of stents. Minimally invasive interventions are also being used increasingly in biopsies, spinal therapy and tumor ablations.

During the course of a minimally invasive intervention one or more medical instruments for example are inserted into the body of a patient for therapeutic or diagnostic purposes. Once a medical instrument has been inserted into the body of the patient it is no longer optically visible to a physician carrying out the intervention. To navigate the instrument in the body of the patient said instrument must therefore be visualized in image information in an appropriate manner for the physician. Different types of systems and methods are currently available for determining the position of the instrument in the body of the patient during minimally invasive medical interventions, as required for the visualization of the instrument, in particular the tip of the instrument, in image information from the inside of the body of the patient.

Progress in 3D x-ray imaging now allows 3D mapping of organs and also instruments in the body of a living being. However it is still difficult to distinguish between instruments, organs and bones in the x-ray image, while at the same time using as little x-ray radiation as possible for imaging and for determining the position of instruments.

SUMMARY OF INVENTION

In this context a method for determining the position and orientation of an object, in particular a catheter, in a patient from two-dimensional x-ray images by means of so-called template matching is described in DE 10 2005 028 746 A1. Here a three-dimensional template of the catheter is generated based on the known structural properties of the catheter. To determine the position and orientation of the catheter in the body of a living being the three-dimensional template is projected onto a two-dimensional plane and the generated projection image is compared with an x-ray image, in which the catheter is mapped. Initially established parameters for the position and orientation of the template in space are then modified iteratively and a degree of similarity is determined, which is used to determine the position and orientation of the catheter.

An electromagnetic navigation system AURORA from NDI, Waterloo, Ontario, Canada is described in "Needle and catheter navigation using electromagnetic tracking for computer-assisted C-arm CT interventions", Markus Nagel, Martin Hoheisel, Ralf Petzold, Willi A. Kalender and Ulrich H. W. Krause, Medical Imaging 2007: Visualization and Image-Guided Procedures, edited by Kevin R. Cleary, Michael I. Miga, Proc. of SPIE Volume 6509, 65090J, (2007)•1605-7422/07/$18•doi: 10.1117/12.709435. The electromagnetic navigation system comprises a field generator for generating an electromagnetic field, to determine positions and orientations of medical instruments, each having small induction coils at their tip. The AURORA system uses the induced voltages to determine the position and orientation of the respective instrument.

To improve the accuracy of instrument location and to improve the determination of coordinate transformations between an image coordinate system and a navigation system assigned to the navigation system, which is also referred to as registration, navigation systems based on x-ray radiation and/or on electromagnetic waves frequently have a plate comprising x-ray markers and/or electromagnetic markers, which is arranged beneath a patient, on whom the minimally invasive intervention is being carried out. Thus the system described in "Needle and catheter navigation using electromagnetic tracking for computer-assisted C-arm CT interventions", Markus Nagel, Martin Hoheisel, Ralf Petzold, Willi A. Kalender and Ulrich H. W. Krause, Medical Imaging 2007: Visualization and Image-Guided Procedures, edited by Kevin R. Cleary, Michael I. Miga, Proc. of SPIE Volume 6509, 65090J, (2007) •1605-7422/07/$18•doi: 10.1117/12.709435, has a so-called registration panel with five x-ray markers, which can be detected automatically in x-ray images, and with an electromagnetic sensor, which can be detected using the AURORA system. The registration panel here is not only used for registration but also as a reference system during the navigation of instruments.

One disadvantage of this solution is that the plate comprising x-ray markers and/or electromagnetic markers or the registration panel is uncomfortable for the patient and the patient can experience bruises or pressure sores during the course of longer interventions.

The object of the invention is therefore to avoid such discomfort for the patient as far as possible.

According to the invention this object is achieved by a medical cushion for assisting with the navigation of a medical object in the body of a patient, having at least one x-ray positive and at least one electromagnetic marker and a soft filler material that yields to the force exerted by the weight of the patient and molds itself at least to some extent to the surface of the body of the patient, with the filler material being arranged in the cushion in such a manner that it lies between the surface of the body of the patient and the at least one x-ray positive and the at least one electromagnetic marker when the cushion is in use. It is proposed therefore that at least one x-ray positive and at least one electromagnetic marker be integrated in a medical cushion, their relative position to one another being known, with the filler material being present in particular on the side of the cushion facing toward the surface of the body of the patient. This allows the patient to be supported in a relatively comfortable manner with the cushion between them and the patient table, so that bruises to the body of the patient and/or pressure sores on the body of the patient due to the at least one x-ray positive and the at least one electromagnetic marker are avoided. The side of the cushion facing away from the surface of the body of the patient does not have to contain the filler material. However it should then be possible to identify the side of the cushion intended to face toward the surface of the body of a patient and the side of the cushion intended to face away from the surface of the body of a patient by corresponding marking.

A support cushion made of foam material with reference bodies for use in a computed tomography system is also known from DE 84 11 550 U1, the reference bodies with their known attenuation coefficients allowing automatic adaptive control of the computed tomography system with each measurement.

A support mat for a patient to be examined using computed tomography is described in DE 100 52 193 A1. The support mat has recesses for reference bodies on its underside, said reference bodies being made from a defined material, so that density values of the bone material of a patient can be determined.

A patient support surface for automatic, intraoperative registration of image data records is known from DE 10 2005 006 775 A1. The patient support surface has reference elements for this purpose, which can be identified automatically in image data. The reference elements can be arranged for example in lateral rails and configured as hollow chambers, which can be filled specifically with air or a contrasting material, e.g. aluminum or titanium rods. The reference elements are determined in different image data records and the image data records can then be registered with one another.

A reference phantom for quantitative computed tomography is described in U.S. Pat. No. 4,870,666, having a flexible comparison facility with means for allowing the reference phantom to be brought into contact with the curved surface of the pelvic region of a patient. The reference phantom is initially curved more than necessary, so that the pressure of the weight of a patient extends the reference phantom, thereby achieving good contact along the pelvic region of the patient. The reference phantom can contain reference bodies, which attenuate x-ray beams, for comparative measurements.

A medical pelvis positioning and tracking apparatus with three pelvic support elements is known from US 2008/0009713 A1, being arranged on a patient support apparatus. A magnetic field generator of an electromagnetic tracking system is arranged in or on one of the pelvic support elements, to generate an electromagnetic field for navigation in the pelvic region.

According to one variant of the invention the at least one x-ray positive and the at least one electromagnetic marker are surrounded by the filler material. The medical cushion therefore has filler material on both sides, so there is no need to identify the sides.

According to one embodiment of the invention the filler material of the medical cushion is a formable and/or elastic foam material or a gel-type liquid.

In one variant of the invention the medical cushion has an outer protective cover, which is intended in particular to prevent the penetration of external bodies or external media into the medical cushion. The outer protective cover preferably prevents the passage of liquids.

According to a further variant of the invention the outer protective cover of the medical cushion is made of a non-slip material, e.g. a rubber-type or silicone-type material. This allows the cushion to be fixed in relation to a patient and/or in relation to a patient support apparatus.

Alternatively or additionally the outer protective cover of the medical cushion has detachable fixing means on at least one side, preferably on the side facing away from the surface of the body of the patient. The detachable fixing means of the medical cushion preferably comprise at least one inherent bonding surface and/or at least one surface having barbs or loops forming part of a Velcro-type fastener. In the case of the bonding surface the cushion can be bonded temporarily to a patient and/or to a patient support for fixing purposes. In the case of a Velcro-type fastener the outer protective cover of the cushion has a surface comprising barbs for example and the patient support apparatus has a surface comprising loops for example, so that the cushion can likewise be fixed temporarily on the patient support apparatus. The respective surfaces can be essentially separate small points, circular, rectangular, strips, etc. As mentioned above, the connections can be detached easily in each instance.

In one embodiment of the invention the at least one x-ray positive marker has a diameter of approximately 3 to 15 mm. The x-ray positive marker here can be spherical, cylindrical, annular, disk-shaped, etc. The at least one x-ray positive marker is preferably made at least partially of lead.

According to a further embodiment of the invention the at least one electromagnetic marker of the medical cushion has at least four, preferably six, receive coils with different spatial alignments in relation to one another and therefore at least four or six degrees of freedom.

According to one variant of the invention the at least one x-ray positive marker and the at least one electromagnetic marker of the medical cushion are arranged on or in a carrier material, which is surrounded for example by the filler material. The carrier material can be an epoxy resin for example.

According to a further variant of the invention the medical cushion has at least one interface for electrical contacting of the at least one electromagnetic marker. An interface here also refers to an electrical connection for electrical contacting of the at least one electromagnetic marker.

According to one embodiment of the invention the medical cushion can be sterilized, preferably in an autoclave.

According to another embodiment of the invention the medical cushion can however also be provided for single use.

According to variants of the invention the medical cushion has a length of approximately 50 to 200 mm, a width of approximately 50 to 150 mm and/or a height of approximately 3 to 20 mm.

BRIEF DESCRIPTION OF THE DRAWINGS

One exemplary embodiment of the invention is illustrated in the accompanying schematic drawings, in which:

FIG. 2 shows a sectional representation of an inventive medical cushion and

FIG. 3 shows a view of the section in the direction of the arrows III from FIG. 2.

DETAILED DESCRIPTION OF INVENTION

Figure 1:
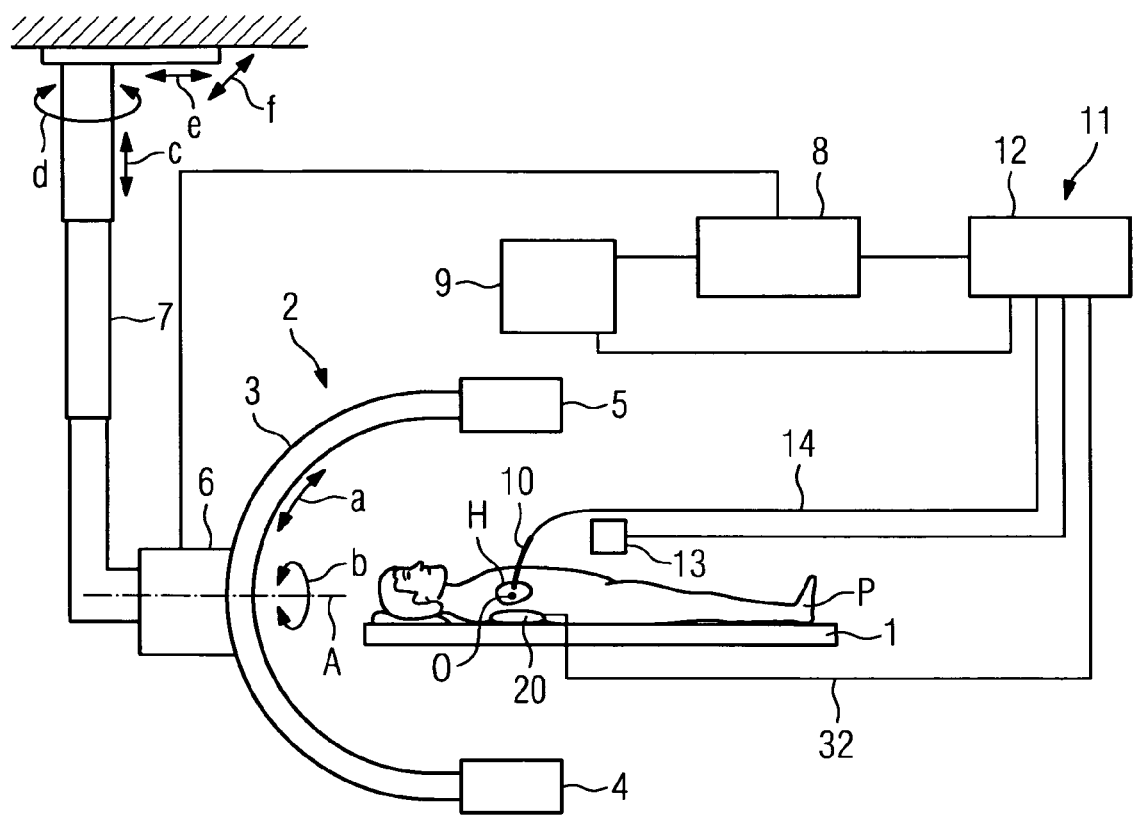
FIG. 1 shows a facility for carrying out catheter navigation on a patient.

FIG. 1 shows a facility for carrying out catheter navigation on a patient P supported on a schematically illustrated patient couch 1.

The facility comprises a C-arm x-ray device 2 with a C-arm 3, on which an x-ray beam source 4 and an x-ray beam detector 5 are arranged opposite one another. The C-arm is supported on a support 6 so that it can be adjusted about its orbital axis O in the directions of the double arrow a. In the present exemplary embodiment the support 6 is arranged on a ceiling gantry 7, which offers the adjustment options shown in FIG. 1 with double arrows c, d, e and f for the support 6 provided with the C-arm 3. The C-arm 3 can also be adjusted with the support 6 about its angulation axis A in the directions of the double arrow b.

The C-arm x-ray device 2 can be used in the manner known per se to record 2D x-ray projections or fluoroscopy images of the patient P supported on the patient couch 1 from different projection directions, it being possible then to display these on a display device 9 connected to an image processor 8. The C-arm x-ray device 2 can also be used to reconstruct 3D images of the inside of the body of the patient P using the image processor 8 from 2D x-ray projections recorded from different projection directions and display them on the display device 9.

In the present exemplary embodiment image information obtained using the C-arm x-ray device is to be used to carry out catheter navigation at the heart H of the patient P, during the course of which a catheter 10 is inserted into the body of the patient P, advanced to the heart H of the patient P and deployed there to carry out treatment on the heart H.

To this end the facility in FIG. 1 also has an electromagnetic navigation system 11. In the present exemplary embodiment the electromagnetic navigation system 11 comprises a control and computation unit 12, to which a transmitter or field generator 13 is connected to generate an alternating electromagnetic field. To this end the field generator 13 is arranged in proximity to the heart H of the patient P. The navigation system also comprises small coils, which are known per se and not specifically illustrated and which are arranged in or on the tip of the catheter 10 and are connected to the control and computation unit 12 by means of lines combined together in a cable 14. The electromagnetic field of the field generator 13 induces voltages in the small coils of the catheter 10, which are measured using the control and computation unit 12 and used to determine the position and orientation of the tip of the catheter 10 in a coordinate system assigned to the navigation system.

To overlay an image of at least the tip of the catheter 10 in an image of the inside of the body of the patient P obtained using the C-arm x-ray device 2 and thus to assist with catheter navigation, a patient or image coordinate system and the coordinate system of the navigation systems, in which the coordinates of the tip of the catheter 10 are determined, must be registered with one another.

To this end in the present exemplary embodiment an inventive flat medical cushion 20, as shown in FIG. 2, is used for example. For catheter navigation at the heart H of the patient P the cushion 20 is arranged beneath the patient P in the region of the heart H in the image recording region of the C-arm x-ray device 2.

As shown in FIGS. 2 and 3, in the present exemplary embodiment the cushion 20 has a plate-type carrier material 21, in which are embedded five x-ray positive spherical markers 22, preferably containing lead. The markers 22 have a diameter of approximately 3 to 15 mm and can be identified clearly in x-ray images. In the present exemplary embodiment an electromagnetic marker 23 having six receive coils (not specifically shown) with different spatial alignments in relation to one another, in other words six degrees of freedom, is also embedded in the carrier material 21. The location of the five x-ray positive markers 22 and of the electromagnetic marker 23 in relation to one another is then known.

In the present exemplary embodiment the carrier material 21 having the markers is surrounded completely by a soft filler material, which yields to the force exerted by the weight of the patient P and molds itself at least to some extent to the surface of the body of the patient P, in the form of a formable and elastic foam material 24. The cushion 20 also has an outer protective cover 25, which is intended to prevent the ingress of external bodies and external media. The outer protective cover is in particular embodied to prevent the passage of liquids.

To prevent the cushion 20 slipping during use, in the present exemplary embodiment the outer protective cover 25 is made from a non-slip material, e.g. rubber or silicone. Alternatively or additionally the outer protective cover 25 can have detachable fixing means. These can be at least one inherent bonding surface. FIG. 3 shows two bonding surfaces 26, 27 by way of example. While the bonding surface 26 serves to fix the cushion 20 to the patient couch 1, the bonding surface 27 is used to fix the cushion 20 to the back of the patient P. The bonding surfaces can be detached again from the patient P or the patient couch 1 in a simple manner at any time.

The detachable fixing means can however also comprise at least one part of a Velcro-type fastener. FIG. 3 by way of example shows a surface 28 on the underside of the cushion 20, which is part of a Velcro-type fastener and has barbs. The associated counterpart of the Velcro-type fastener, namely a surface 29 with loops, is attached to the patient couch 1, as shown schematically in FIG. 3. By arranging the surface 28 having barbs on the surface 29 having loops it is thus likewise possible to fix the cushion 20 temporarily on the patient couch 1.

The cushion here can have all the forms of temporary fixing, in other words outer protective cover made of a non-slip material, bonding surface, Velcro-type surface, or just one or two of these fixing forms or means.

For electrical contacting of the electromagnetic marker 23 the cushion 20 also has an interface or connection 30, which is connected to the electromagnetic marker 23 by way of a cable 31. The cushion 20 is connected to the control and computation unit 12 of the navigation system using a cable 32 as shown in FIG. 1.

The cushion 20 can preferably be sterilized and can thus be re-used. However the cushion 20 can also be provided just for single use, in particular in the embodiment with an inherent bonding surface.

The cushion 20 preferably has a length L of approximately 50 to 200 mm, a width B of approximately 50 to 150 mm and a height H of approximately 3 to 20 mm auf.

The required registration of the navigation system 11 and the C-arm x-ray device 2 can take place with the aid of the cushion 20, in order to be able to overlay images of the tip of the catheter 10 in images of the inside of the body of the patient P obtained using the C-arm x-ray device 2 with the correct position and orientation to assist navigation. The cushion 20 with the markers 22, 23 can however also be used as a reference system during navigation.

After x-ray images are recorded of the body region of the patient P containing the heart H, in which the x-ray positive markers 22 are also mapped, said images are forwarded to the control and computation unit 12 of the navigation system. The software of the control and computation unit 12 analyzes the x-ray images and carries out registration automatically. Actual catheter navigation starts after registration Using the cushion 20 allows the patient P to be supported in a relatively comfortable manner on the patient couch 1, thereby ensuring that the patient P does not experience bruises or pressure sores.

In contrast to the described exemplary embodiment the cushion may also only have filler material on the side facing toward the body of the patient. Materials other than those mentioned can also be used as the filler material.

The cushion can also have more or fewer x-ray positive markers and/or more electromagnetic markers. Depending on the application the cushion may also have only at least one x-ray positive or only at least one electromagnetic marker.

The invention claimed is:

1. A medical cushion, comprising:
an x-ray positive and an electromagnetic marker; and
a soft filler material;

wherein the soft filler material yields to a force exerted by a weight of a patient and at least partially molds to a surface of the body of the patient, and wherein the soft filler material is arranged in the cushion such that it lies between the surface of the body of the patient and the x-ray positive and the electromagnetic marker when the cushion is in use.

2. The medical cushion as claimed in claim 1, wherein the x-ray positive and the electromagnetic marker are surrounded by the soft filler material.

3. The medical cushion as claimed in claim 2, wherein the x-ray positive marker and the electromagnetic marker are arranged on or in a carrier material.

4. The medical cushion as claimed in claim 1, wherein the soft filler material is a formable and/or elastic foam material or a gel-type liquid.

5. The medical cushion as claimed in claim 1, further comprising an outer protective cover wherein the outer protective cover prevents a passage of liquids.

6. The medical cushion as claimed in claim 5, wherein the outer protective cover is made from a non-slip material.

7. The medical cushion as claimed in claim 5, wherein the outer protective cover has a plurality of detachable fixing areas on at least one side of the medical cushion.

8. The medical cushion as claimed in claim 7, wherein the plurality of detachable fixing areas comprise an inherent bonding surface and/or a surface having barbs or loops forming part of a Velcro-type fastener.

9. The medical cushion as claimed in claim 1, wherein the x-ray positive marker has a diameter of approximately 3 to 15 mm.

10. The medical cushion as claimed in claim 1, wherein the at x-ray positive marker comprises lead.

11. The medical cushion as claimed in claim 1, wherein the electromagnetic marker has at least four receive coils with different spatial alignments in relation to one another.

12. The medical cushion as claimed in claim 1, wherein the at least one electromagnetic marker has six receive coils with different spatial alignments in relation to one another.

13. The medical cushion as claimed in claim 1, further comprising an interface for an electrical connection of the electromagnetic marker.

14. The medical cushion as claimed in claim 1, wherein the medical cushion is sterilized.

15. The medical cushion as claimed in claim 1, wherein the medical cushion is provided for a single use.

16. The medical cushion as claimed in claim 1, wherein the medical cushion has a length of approximately 50 to 200 mm.

17. The medical cushion as claimed in claim 1, wherein the medical cushion has a width of approximately 50 to 150 mm.

18. The medical cushion as claimed in claim 1, wherein the medical cushion has a height of approximately 3 to 20 mm.

19. The medical cushion as claimed in claim 1,
wherein the cushion assists with the registration of the navigation system and the C-arm x-ray device, and
wherein the medical cushion assists as a reference system during navigation.

* * * * *